United States Patent [19]

Karakelle et al.

[11] Patent Number: 4,990,357

[45] Date of Patent: Feb. 5, 1991

[54] ELASTOMERIC SEGMENTED HYDROPHILIC POLYETHERURETHANE BASED LUBRICIOUS COATINGS

[75] Inventors: Mutlu Karakelle, Dayton; Houshang Karimi, Kettering; Min-Shui Lee, Spring Valley; Robert A. Taller, Centerville, all of Ohio

[73] Assignee: Becton, Dickinson and Company, Franklin Lakes, N.J.

[21] Appl. No.: 347,133

[22] Filed: May 4, 1989

[51] Int. Cl.$^5$ ............................................. A01N 1/02
[52] U.S. Cl. .................................... 427/2; 427/353; 427/430.1; 523/105; 525/125
[58] Field of Search .............. 427/2, 336, 430.1, 353; 523/112, 113; 105; 604/265; 525/125

[56] References Cited

U.S. PATENT DOCUMENTS

| | | | |
|---|---|---|---|
| 4,062,834 | 12/1977 | Gilding et al. | 260/77.5 AA |
| 4,100,309 | 7/1978 | Micklus et al. | 427/2 |
| 4,160,076 | 7/1979 | Guthrie et al. | 521/159 |
| 4,373,009 | 2/1983 | Winn | 428/424.2 |
| 4,377,010 | 3/1983 | Fydelor et al. | 210/500.39 |
| 4,642,267 | 2/1987 | Creasy et al. | 428/413 |
| 4,720,521 | 1/1988 | Spielvogel et al. | 524/862 |
| 4,767,414 | 8/1988 | Williams et al. | 604/230 |
| 4,795,475 | 1/1989 | Walker | 106/287.23 |
| 4,906,240 | 3/1990 | Reed et al. | 604/307 |

OTHER PUBLICATIONS

Hypol TM, W. R. Grace and Company, 55 Hayden Avenue, Lexington, MA–product brochure.

*Primary Examiner*—Michael Lusignan
*Attorney, Agent, or Firm*—Richard E. Brown

[57] ABSTRACT

A coating composition for an article surface includes a uniform blend of an elastomeric segmented hydrophilic polyetherurethane and a hydrophilic polymer, such as polyvinylpyrrolidone. The invention includes a method for rendering an article surface lubricious which includes coating the composition onto the article surface and contacting the coated surface with an aqueous liquid.

16 Claims, No Drawings

ELASTOMERIC SEGMENTED HYDROPHILIC POLYETHERURETHANE BASED LUBRICIOUS COATINGS

BACKGROUND OF THE INVENTION

1. Field of the Invention

This invention relates to lubricated surfaces. More particularly, the invention relates to a coating for a surface which is lubricious and biocompatible when in contact with a body fluid, and to a method for preparing same.

2. Background

Many articles, devices and products require a lubricated surface. In the medical instrumentation and diagnostic field, simple sensing devices such as, for example, thermometers and needles, or electrode components of complex monitoring apparatuses, must be inserted into a body cavity or through the skin and at a later time withdrawn. Patient treatment often includes catheterization procedures or nutrition delivery systems, most of which involve invasive techniques. In all such cases, effective lubrication which is stable throughout both the insertion and withdrawal stages of the procedure contributes greatly to patient comfort.

Many medical devices are fabricated from glass or polymeric materials such as polypropylene, polyvinyl chloride, polytetrafluoroethylene and polyurethane. Such materials are for the most part inherently nonlubricious. A variety of approaches to introduce lubricity have been advanced. Simple coatings of lubricants such as mineral oils or silicones to glass or polymeric surfaces are generally unsatisfactory because the surface energy is too low and the lubricant tends to migrate or "bead." A method to overcome migration of silicone lubricants is described by Williams et al. in U.S. Pat. No. 4,767,414. A surface to be lubricated is coated with silicone oil and both the surface and oil are subjected to an ionizing plasma.

Spielvogel et al., in U.S. Pat. No. 4,720,521 teaches adherence of a lubricating composition to a surface. The composition includes a polysiloxane lubricant entrapped in a mixture of a plurality of reactive silicone components which, on curing, adhere to the surface.

Thermoplastic polyurethanes prepared from polyisocyanates, high molecular weight polyetherglycols, and low molecular weight diols and diamines as chain extenders are conventionally referred to as polyetherurethanes, and this term, will be used in this disclosure for polyurethanes having a polyether backbone.

Polyetherurethane compositions develop microdomains conventionally termed hard segment domains and soft segment domains and are often referred to as segmented polyurethanes. They are (AB)n type block copolymers, A being the hard segment and B the soft segment. The hard segment domains form by localization of the portions of the copolymer molecules which include the isocyanate and extender components whereas the soft segment domains form from the polyether glycol portions of the copolymer chains. The phase seperated microdomain structure forms if the hard segments of polyetherurethane chain are a certain size. A long hard segment promotes the phase separated microdomain structure. Conversely, non extended formulations (those lacking an extender) have very short hard segments and minimum phase seperated microdomain structure. The hard segment is crystalline and provides physical crosslinking and reinforcement. The polyether glycol soft segment is mostly in a rubbery state and provides elasticity. Therefore, polyetherurethanes are thermoplastic elastomeric materials. A wide range of physical properties can be obtained by altering the relative ratios of the hard and soft segments. The elasticity, toughness and other desirable properties of polyetherurethanes are the result of their phase seperated microdomain structure.

Elastomeric segmented polyurethanes have particular advantages for fabrication of medical devices, as discussed by Gilding et al. in U.S. Pat. No. 4,062,834 but have limited inherent lubricity. Micklus et al. in U.S. Pat. No. 4,100,309 teaches a lubricious polyurethane-polyvinylpyrrolidone (PVP) interpolymer coating which may be applied to a polymeric article by dipping the article into a solvent solution of polyurethane and a polyisocyanate to give an isocyanate-containing prepolymer on the article surface and dipping the prepolymer-coated article into a solution of PVP.

In U.S. Pat. No. 4,373,009 to Winn, a substrate surface is primed with a polyisocyanate as shown by Micklus et al., and the isocyanate groups are covalently bonded to active hydrogens of a hydrophilic copolymer, such as a copolymer of PVP and acrylamide. A coating which is stable and resistant to removal, in contrast to prior art coating, is claimed.

U.S. Pat. No. 4,642,267 to Creasy et al. describes lubricious coatings which are alloys or blends of PVP and polyurethanes lacking both free isocyanate groups and chain extenders.

Although the above disclosures have advanced the art of rendering surfaces lubricious, there remains a need for a coating which is instantly lubricious, easily applied and strongly adherent so as to remain on the substrate to which it is applied with no tendency to wash off or separate as solid flakes on prolonged contact with liquids.

SUMMARY OF THE INVENTION

One aspect of the present invention is a coating composition for articles which includes a uniform blend of a hydrophilic polymer and an elastomeric segmented hydrophilic polyetherurethane (HPEU). Preferred compositions are blends of PVP and a diol extended HPEU which includes polyethyleneoxide as the soft segment. The most preferred composition has a hard segment content of about 35 to 45%.

Another aspect of the invention is a method to render the surface of an article lubricious by coating the surface with the composition of the invention. Preferably, the article is dipped into a solution of the composition in an appropriate solvent and the solution then evaporated. The article thus coated with the composition is brought into contact with a liquid, preferably an aqueous liquid, whereby the article surface is rendered lubricious. Most preferably, a medical device, such as a catheter, is coated with the composition.

In accordance with the invention, the surface of a medical article is rendered instantly lubricious when coated with the composition and wetted with an aqueous liquid or water. The composition adheres firmly to the surface of the article through the HPEU component. The PVP component is trapped in the HPEU matrix as a result of strong hydrogen bonding and migrates slowly to the surface of the HPEU when the composition is in contact with the liquid. The mobile PVP on the surface is believed to account for the outstanding lubricity of articles coated with the composition. Because the migration is slow, the article remains lubricious for prolonged times.

In particular, the inclusion of the elastomeric segmented HPEU provides hard segments through which exceptionally strong hydrogen bonding to the article surface are formed so that there is no tendency for the coating to separate from the surface, even under conditions of exposure to flowing liquids, as blood. Further, the elastomeric segmented HPEU having phase separated microstructure contributes to a surface having a high level of biocompatibility, in particular excellent blood compatibility and thus very low thrombogenicity and very low toxicity.

DETAILED DESCRIPTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments described. The scope of the invention will be measured by the appended claims and their equivalents.

In this disclosure the following abbreviations are used:
PEG-polyethyleneoxide glycol
PU-polyurethane
PEU-polyetherurethane
PVP-polyvinylpyrrolidone
HPEU-hydrophilic polyetherurethane
PVC-polyvinyl chloride
MDI-4,4'-diphenylmethane diisocyanate
PEO-polyethyleneoxide (molecular weight of 100,000 or higher)
BDO-1,4 -butanediol
DMF-dimethylformamide
DMAC-dimethylacetamide
NMP-methylpyrrolidone
MEK-methyl ethyl ketone
THF-tetrahydrofuran
DEA-diethyl ethanolamine
TEA-triethylamine
DAA-diacetone alcohol
NEPEU-nonextended polyetherurethane
NEHPEU-non extended hydrophilic polyether-urethane
HS-hard segment In accordance with the present invention, it has been found that HPEUs have many salubrious properties which make them attractive as base materials in lubricious coatings. Particularly useful are elastomeric segmented HPEUs which adhere well to a variety of substrates and provide exceptional properties not shown by linear, non extended PUs.

The hard segment-soft segment ratio greatly influences the properties of a HPEU and may be varied over a wide range by varying the proportions of the polyisocyanate, polyetherglycol and extender included in the formulation. HPEUs of low hard segment content are generally soft, of low mechanical strength and absorb water to such an extent that they are poorly adherent when coated on most polymeric substrates. On the other hand, HPEUs of high hard segment content have a high degree of crystallinity and are strongly adherent to polymeric substrates but the pronounced phase separation reduces the ability of the base HPEU to blend well with lubricious components.

The present invention provides a method for coating a polymeric substrate with a composition which gives a stable lubricious substrate surface when the substrate comes into contact with a liquid. The composition of the invention includes an elastomeric segmented HPEU and a hydrophilic polymer.

A variety of substrates is contemplated to be coated with the PU composition of the invention. The substrate may, for example, be glass, metal such as steel, or preferably a polymer. Preferred polymeric substrates are polytetrafluoroethylene, polyester, polyamide, PVC, polyacrylate, polystyrene, latex rubber and, most preferably PU. Most preferably, a PVC or PU substrate is shaped into the form of a desired medical article, such as a catheter tubing, and the composition of the invention coated onto the shaped article.

HPEUs suitable for use as the base component of the coating composition of present invention include three essential components, a diisocyanate, a polyether glycol and a chain extender. Suitable diisocyanates are aromatic diisocyanates such as MDI, alicyclic diisocyanates such as isophorone diisocyanate and 4,4'-dicyclohexylmethane diisocyanate, and aliphatic diisocyanates, as, for example, hexamethylene diisocyanate. The most preferred diisocyanate is MDI.

The polyether glycol component may be PEG, alone or mixed with polypropyleneoxide glycol or polytetramethyleneoxide glycol. The preferred polyol is PEG having a molecular weight of from about 600 to 3300, or a mixture containing 50% or more by weight thereof. The most preferred polyether glycol is a PEG having an average molecular weight of 1000 to 1450.

The chain extender may be water and/or a low molecular weight branched or unbranched diol, diamine or aminoalcohol of up to 10 carbon atoms or mixtures thereof. Representative nonlimiting examples of chain extenders are BDO; ethylene glycol; diethylene glycol; triethylene glycol; 1,2-propanediol; 1,3-propanediol; 1,6-hexanediol; 1,4-bis-hydroxymethyl cyclohexane, hydroquinone dihydroxyethyl ether, ethanolamine, ethylenediamine and hexamethylenediamine. Preferred chain extenders are 1,6-hexanediol, ethylenediamine hexamethylenediamine and, most preferably, BDO.

The percentages of the components may be such that the hard and soft segments of the composition may be from about 25 to 60 and from about 40 to 75, preferably from about 30 to 50% and 50 to 70% respectively of the total weight of the formulation. From these percentages and ratios, suitable proportions of the components may readily be calculated. Representative elastomeric segmented HPEU base components are listed in Table I of Example I below.

The HPEU base component of the composition may be prepared by solution or bulk synthesis methods. Example I provides typical procedures, however, various modifications of this conventional procedure are well known to those skilled in the art. Alternatively, the HPEU may be prepared by conventional emulsion polymerization, in water, to give an HPEU latex.

A feature of the method for preparing the HPEU formulations of the invention is that the polymers are prepared from the components without adding a polymerization catalyst. Conventional catalysts in the art, for example, organometallic compounds such as dibutyl tin dilaurate, are leachable and may cause deleterious effects in blood-contacting elements fabricated from prior art catalyst-containing HPEU. By avoiding use of a catalyst, HPEUs of the invention are purer and potentially less toxic than those of the prior art.

A second component of the coating composition of the present invention is a water soluble hydrophilic polymer. Exemplary of suitable hydrophilic polymers are polyacrylic acid, polyvinyl pyridine, polyvinylmethyl ether, polyhydroxyethyl methacrylate, PEO and, preferably PVP. While the PVP of the invention may be of any suitable molecular weight, it is preferred to use a PVP having a molecular weight of about 10,000 to 1,000,000.

The coating composition of the present invention may be prepared by mixing the HPEU and PVP components in a suitable solvent wherein the ratio of HPEU to PVP may be from about 25 to 0.05, preferably about 4 to 0.25 parts by weight. In the most preferred composition, 1 part of HPEU and 1 part of PVP are mixed. Suitable solvents are DMAC, DMF, and the composition may be about 1 to 20, preferably about 4 to 12% by weight in the solvent.

The composition dissolved in the solvent may be applied to the substrate surface by any suitable method such as brushing, spraying or, preferably continuous dip coating. The substrate may be dipped into the solvent solution of the composition at any suitable temperature up to the boiling point of the solvent. The dipping procedure may preferably be carried out at ambient temperature for a time of 1 sec. up to 30 minutes. Dipping is preferably carried out for about 1 to 30 seconds. After the dipping process is complete, the solvent may be removed, under forced evaporation at ambient temperature, preferably by warming the coated substrate in an oven at about 50° C. to 200° C.

Depending on the intended use, other components may be incorporated into the coating composition of the invention in order to achieve particular properties. For example additives such as flow aids, flatting agents, plasticizers, heat stabilizers and surface cure modifiers may be added to the formulation prior to prepolymer formation, prior to conversion of the prepolymer to the HPEU, or preferably directly to the solvent solution of the components prior to coating. Such additives and their use to modify polymer properties are conventional and well known to those skilled in the art.

Particularly preferred is addition of an antimicrobial agent to the coating composition. Any antimicrobial agent which is substantially stable and which may be released slowly from the coating may be used. Exemplary of suitable antimicrobial agents are povidone iodine, chlorohexidene or chlorohexidene iodine complex. The quantity of antimicrobial agent to be added may be from about 1 to 10, preferably 2 to 6 weight percent.

The substrate coated with the composition of the invention is dry and nonsticky to the touch until wet with a liquid, at which time it develops a slippery lubricious feel. It is believed, although as yet unsubstantiated, that the preferred coating of the invention includes strong hydrogen bonding between the HPEU and PVP chains so that the chains of PVP are substantially trapped in the HPEU base polymer without actually being chemically linked thereto. This arrangement of the two polymers provides the coating with the mechanical strength and bonding capability of segmented PUs yet leaves the PVP molecules unattached so that slow diffusion of the hydrophilic polymer to the surface of the coated substrate may take place.

The coating composition of the invention is particularly useful when applied to medical devices. For example, a catheter coated with the composition becomes instantly lubricious when it comes into contact with water or a body fluid such as blood and thereby contributes greatly to the comfort of a patient undergoing catheterization. One skilled in the art will immediately recognize other medical devices, such as nutrition delivery systems, cannulas, needles, thermometers, urethral catheters and various components of medical monitoring apparatuses which may advantageously be coated with the composition of the invention.

Representative coating compositions of the invention are listed in Table II of Example II. The coatings of the invention were applied to a polymeric substrate by the procedure of Example III and tested for stability as described in Example IV and were found to be substantially more stable than coatings prepared from prior art PUs.

Substrates coated with the composition of the invention are substantially dry until contacted with a liquid whereupon they are instantly rendered lubricious. Lubricity of the coated surfaces were determined by measuring their coefficients of friction using the Instron Model 1122 Universal Testing Machine by the procedure described in Example V. Lubricity data is given in Table II which accompanies Example II.

The following examples are given to further illustrate the invention but are not to be considered as limitative thereof.

EXAMPLE I

Bulk Synthesis

PEG was dried at 60° to 70° C. under vacuum (4–6 mm Hg) for 4 to 6 hours to remove moisture. Water content (Carl Fisher titration) and polyol hydroxyl number (phthalic anhydride pyridine method) were determined to adjust formulation stoichiometry. MDI was filtered to remove any reacted diisocyanate and vacuum stripped (4–6 mm Hg) for 2 to 4 hours. The stoichimetric amounts of PEG and BDO were placed in the polymerization vessel and degassed at 60° for 30 minutes. Then, the stoichiometric amount of MDI (1.02 index) was added and the mixture stirred vigorously until the polymerization temperature reached about 85° to 90° C. The polymer was discharged and postcured at 125° C. for 30 minutes.

Solution Synthesis

Solution polymerization at 25% total solids was performed in DMAC under a nitrogen atmosphere. PEG was dried at 60° to 70° C. under vacuum (4–6 mm Hg) for 4 to 6 hours to remove moisture. Water content (Carl Fisher titration) and polyol hydroxyl number (phthalic anhydride pyridine method) were determined to adjust formulation stoichiometry. MDI was filtered to remove any reacted diisocyanate and vacuum stripped (4–6 mm Hg) for 2 to 4 hours. Stoichiometric amounts of PEG and BDO were placed in the polymerization vessel and degassed at 60° C. for 30 minutes. Two thirds of the total solvent used (DMAC) was added to the PEG-extender mixture. The stoichiometric (1.02 Index) amount of MDI was dissolved in the remaining DMAC and the solution was added dropwise to the polymerization vessel. The polymerization medium was maintained at 60° to 70° C. and constantly stirred. A polymerization time of four hours at 60° to 70° C. was sufficient for adequate formation.

TABLE I

Typical HPEUs of the Invention

| HPEU NO. | HS CONTENT (% WT) | POLYETHER TYPE | NUMBER OF EQUIVALENTS OF | | |
|---|---|---|---|---|---|
| | | | MDI | BDO | PEG |
| 1 | 30 | PEG 1450 | 1.02 | 0.506 | 0.494 |
| 2 | 35 | PEG 1450 | 1.02 | 0.597 | 0.403 |
| 3 | 40 | PEG 1450 | 1.02 | 0.667 | 0.333 |
| 4 | 45 | PEG 1450 | 1.02 | 0.738 | 0.262 |
| 5 | 50 | PEG 1450 | 1.02 | 0.772 | 0.228 |
| 6 | 55 | PEG 1450 | 1.02 | 0.821 | 0.179 |
| 7 | 60 | PEG 1450 | 1.02 | 0.845 | 0.155 |

EXAMPLE II

Preparation of Lubricious Coating

The HPEU of Example I was dissolved in DMF and the desired amount of PVP (K-90, Aldrich) was added. The solution concentration and the solvent ratio of the lubricious coating solution were adjusted by adding THF.

TABLE II

Examples of HPEU Based Lubricious Coating Compositions of the Invention

| COMPOSITION NO. | HPEU HS % | HPEU/PVP RATIO | CONCENTRATION (% SOLID) | SOLVENTS & RATIOS | COEFFICIENT* OF FRICTION |
|---|---|---|---|---|---|
| 1 | 40 | 3/7 | 6 | DMF/THF (3/2) | 0.114 ± 0.006 |
| 2 | 40 | 1/1 | 6 | " | 0.118 ± 0.013 |
| 3 | 40 | 3/7 | 10 | " | 0.107 ± 0.004 |
| 4 | 40 | 1/1 | 10 | " | 0.130 ± 0.004 |
| 5 | 50 | 3/7 | 6 | " | 0.108 ± 0.012 |
| 6 | 50 | 3/7 | 10 | " | 0.067 ± 0.007 |
| 7 | 50 | 1/1 | 10 | " | 0.121 ± 0.003 |
| 8 | 60 | 3/7 | 6 | " | 0.094 ± 0.003 |
| 9 | 60 | 3/7 | 10 | " | 0.085 ± 0.003 |
| 10 | 60 | 1/1 | 10 | " | 0.114 ± 0.004 |
| PVC CONTROL (UNCOATED FROSTED PVC TUBING) | | | | | 0.986 ± 0.048 |

*Determined by the procedure of Example V.

EXAMPLE III

Coating Application Procedure

The lubricious coatings of this invention were applied to PVC tubing by dip coating. Tubing samples were cut to desired lengths and were heat sealed at one end to contain the coating application to the outer surface only. The thickness of the applied coating was adjusted by changing the dipping rate and the coating solution concentration. The tubing samples were vertically dipped into the coating solutions of Table II (6–10% solids). The coated samples were first placed in a convection oven at 125° C. for 30 seconds, then transferred to another convection oven at 65° C. for 30 to 45 minutes to remove the solvents.

EXAMPLE IV

Lubricious Coating Stability Test

The following tests were employed for determining the stability of the lubricious coatings:
1. The coated tubing samples were placed in distilled water for a few minutes (2 to 5 minutes) and examined visually for signs of delamination. No lubricity testing was performed on samples that delaminated; they were considered unstable.
2. The lubricious coatings that passed the first test were evaluated in the lubricity test. Samples that delaminated during the lubricity test were also considered unstable.
3. Samples that withstood tests 1 and 2, were then tested for the coating adhesion strength as follows: samples were placed in distilled water and vigorously stirred at room temperature for one hour. Samples were visually inspected for lubricious coating delamination.
4. Finally, samples were stored in distilled water at room temperature for 1 to 5 days, then tested for forced delamination by subjecting to the lubricity test. Samples were examined for signs of delamination during the lubricity test.

The lubricious coating stability of the samples that successfully passed test 1 to 4 was rated as excellent. The lubricious coating stability of the samples that failed at any of these four tests were considered unstable.

EXAMPLE V

Lubricity Testing

The lubricity of the disclosed formulations were evaluated by comparing the surface coefficients of friction of the coated samples with that of the uncoated substrate. Surface coefficients of friction were determined using an Instron Universal Testing Machine, Model 1122, and the drag generated between the sample and a natural rubber substrate was measured. Test samples were secured in a water filled trough and were soaked for 5 minutes before testing. A piece of clean natural pure gum rubber (lab grade, Fisher Scientific) was placed in contact with the test sample under water and pulled at a constant speed (5 cm/min) under a standard applied load (532 gm). The measured drag force in newtons (N) was converted to the coefficient of friction (CF) using the following equation:

$$CF = \frac{\text{Drag Force (N)} - \text{Internal Friction (N)}}{0.0098 \text{ (N/gm)} \times \text{Applied Load (gm)}}$$

where the internal friction is the drag generated by the friction apparatus in the absence of sample contact.

EXAMPLE VI

Preparation of Prior Art Coatings and Comparative Study with Coatings of the Invention A. NEPEU Synthesis Polytetramethyleneoxide glycol of 1000 molecular weight, (Terathane 1000, DuPont), was dried at 60° to 70° C. under vacuum (4 to 6 mm Hg) for 4 to 6 hours to remove moisture. MDI was filtered to remove any reacted diisocyanate and vacuum stripped (4 to 6 mm Hg) for 2 to 4 hours. Polyol was weighed and placed in the polymerization vessel. Then the weighed amount of MDI (30%, 40%, 50% by weight) was added, and the mixture stirred vigorously for 15 minutes. The NEPEU thus obtained was stored under nitrogen in a tightly closed jar.

B. NEHPEU Synthesis

PEG of 1450 molecular weight (Union Carbide) was dried at 60° to 70° C. under vacuum (4 to 6 mm Hg) for 4 to 6 hours to remove moisture. MDI was filtered to remove any reacted diisocyanate and vacuum stripped (4 to 6 mm Hg) for 2 to 4 hours. The PEG was weighed and placed in the polymerization vessel, the weighed amount of MDI (40%, 50% by weight) was added, and the mixture stirred vigorously for 15 minutes. The NEHPEU thus obtained was stored under nitrogen in a tightly closed jar.

C. NEPEU and NEHPEU based lubricious coating preparation

The NEPEU and NEHPEU PUs from A and B were dissolved in DMF or DMAC. To this solution a desired amount of PVP (K-90, Aldrich) was added, and the polymer contents were dissolved by constant shaking. The solution concentration and the solvent ratio of the lubricious coating solution were adjusted by adding THF or MEK. The coatings were applied to PVC tubing as described in Example III for stability and lubricity tests.

D. ESTANE 5703 based lubricious coating preparation and application

To a mixture of 75 gm of DAA and 25 gm of MEK were added 4 gm of PVP (K-90, Aldrich) and 2 gm of linear PU (Estane 5703, B.F. Goodrich). The polymer contents were dissolved by constant shaking. The resulting coating solution was applied to PVC tubing using the standard coating application procedure.

E. NEOREZ R940 based lubricious coating preparation and application

To 47 gm of water and 10 gm of NMP were added 10 gm of PVP (K-90, Aldrich) and 33 gm of linear PU aqueous dispersion (Neorez R940, ICI, formerly Polyvinyl Chemical Industries). The polymer contents were dissolved by constant shaking. The resulting solution was applied to PVC tubing using the standard coating application procedure.

The coatings the prior art described in A-E and applied to PVC tubing are listed in Table III as compositions 7-13 and may be compared with compositions 1-6 of the invention.

TABLE III

COMPARATIVE LUBRICIOUS COATING COMPOSITIONS

| COMPOSITION NO. | PU | PU/PVP RATIO | SOL. CONC. (% SOLID) | SOLVENTS AND RATIOS | ADHESION STABILITY | COEFFICIENT OF FRICTION |
|---|---|---|---|---|---|---|
| 1 | HPEU 40% HS | 3/7 | 6 | DMF/THF (3/2) | Excellent | 0.114 ± 0.006 |
| 2 | HPEU 40% HS | 1/1 | 6 | DMF/THF (3/2) | Excellent | 0.118 ± 0.013 |
| 3 | HPEU 40% HS | 3/7 | 10 | DMF/THF (3/2) | Excellent | 0.107 ± 0.004 |
| 4 | HPEU 50% HS | 3/7 | 6 | DMF/THF (3/2) | Excellent | 0.108 ± 0.012 |
| 5 | HPEU 50% HS | 1/1 | 10 | DMF/THF (3/2) | Excellent | 0.121 ± 0.003 |
| 6 | HPEU 50% HS | 3/7 | 10 | DMF/THF (3/2) | Excellent | 0.067 ± 0.007 |
| 7 | ESTANE 5703 | 1/2 | 5.7 | DAA/MEK (3/1) | Unstable | N/A** |
| 8 | NEOREZ R940 | 1/1 | 22 | * | Unstable | N/A |
| 9 | NEPEU-30 | 1/1 | 6 | DMAC/MEK (3/2) | Unstable | N/A |
| 10 | NEPEU-40 | 1/1 | 6 | DMAC/MEK (3/2) | Unstable | N/A |
| 11 | NEPEU-50 | 1/1 | 6 | DMAC/MEK (3/2) | Unstable | N/A |
| 12 | NEHPEU-40 | 1/1 | 6 | DMF/THF (3/2) | Unstable | N/A |
| 13 | NEHPEU-50 | 1/1 | 6 | DMF/THF (3/2) | Unstable | N/A |

*WATER/NMP/MEK/DEA + TEA: (64.8/13.6/0.6/0.7)
**Not attainable - coating delaminated during testing in accordance with Example V.

What is claimed is:

1. A lubricious and biocompatible coating composition for a substrate comprising a substantially uniform blend of a hydrophilic polymer and an elastomeric segmented hydrophilic polyetherurethane which is the reaction product of a diisocyanate, a hydrophilic polyether glycol and a diol chain extender.

2. The composition of claim 1 wherein said polymer is selected from the group consisting of polyhydroxyethyl methacrylate, polyacrylic acid, polyvinylmethyl ether, polyvinylpyridine, polyethyleneoxide and polyvinylpyrrolidone.

3. The composition of claim 1 wherein said diisocyanate is selected from the group consisting of 4,4'-diphenylmethane diisocyanate, 4,4'-dicyclohexylmethane diisocyanate, isophorone diisocyanate and hexamethylene diisocyanate.

4. The composition of claim 1 wherein said hydrophilic polyetherglycol is polyethyleneoxide glycol.

5. The composition of claim 1 wherein the ratio of said hydrophilic polyetherurethane to said hydrophilic polymer is about 25 to 0.05.

6. The composition of claim 1 wherein said diol is selected from the group consisting of ethylene glycol, diethylene glycol, triethylene glycol, 1,2-propanediol, 1,3-propanediol, 1,4-butanediol, 1,6-hexanediol, 1,4-bis-hydroxymethyl cyclohexane and hydroquinone dihydroxyethyl ether.

7. The composition of claim 1 further including a reagent selected from the group consisting of an antimicrobial agent, flow aid, flatting agent, plasticizer, heat stabilizer, and surface cure modifier.

8. The composition of claim 1 wherein said elastomeric segmented polyetherurethane has a hard segment content of about 25 to 60% by weight.

9. A lubricious and hemocompatible coating composition comprising a substantially uniform blend of polyvinylpyrrolidone and an elastomeric segmented hydrophilic polyetherurethane which is the reaction product of 4,4'-diphenylmethane diisocyanate, polyethylene oxide glycol and 1,4-butanediol having a hard segment content of about 25 to 60% by weight.

10. A method for lubricating a polymeric surface comprising coating onto a polymeric surface a composition comprising a substantially uniform blend of a hydrophilic polymer and an elastomeric segmented hydrophilic polyetherurethane which is the reaction product of a diisocyanate, a hydrophilic polyether glycol and a diol chain extender to give a coated surface and contacting said coated surface with a liquid.

11. The method of claim 10 wherein said polymer is selected from the group consisting of polyhydroxyethyl methacrylate, polyacrylic acid, polyvinylmethyl ether, polyvinylpyridine, polyethyleneoxide and polyvinylpyrrolidone.

12. The method of claim 10 wherein said diisocyanate is selected from the group consisting of 4,4'-diphenylmethane diisocyanate, 4,4'-dicyclohexylmethane diisocyanate, isophorone diisocyanate and hexamethylene diisocyanate.

13. The method of claim 10 wherein said hydrophilic polyether glycol is polyethyleneoxide glycol.

14. The method of claim 10 wherein said coating step is performed by dipping.

15. The method of claim 10 wherein said composition further includes a reagent selected from the group consisting of an antimicrobial agent, flow aid, flatting agent, plasticizer, heat stabilizer, and surface cure modifier.

16. A method for lubricating a polymeric surface comprising:
(a) preparing a composition comprising a substantially uniform blend of polyvinylpyrrolidone and an elastomeric segmented hydrophilic polyetherurethane which is the reaction product of 4,4'-diphenylmethane diisocyanate, polyethylene oxide glycol and 1,4-butanediol having a hard segment content of about 25 to 60%;
(b) coating said composition onto a polymeric substrate; and
(c) contacting the coated surface with an aqueous liquid.

* * * * *